(12) United States Patent
Williams et al.

(10) Patent No.: US 7,179,927 B2
(45) Date of Patent: Feb. 20, 2007

(54) EXTRACTION METHOD

(76) Inventors: David Michael Williams, 71 Heol y Coed, Rhiwbina, Cardiff CF14 6HR (GB); Chandra Mohen Pant, 65 King George V Drive, Heath, Cardiff CF4 4EF (GB)

(*) Notice: Subject to any disclaimer, the term of this patent is extended or adjusted under 35 U.S.C. 154(b) by 328 days.

(21) Appl. No.: 10/399,390

(22) PCT Filed: Oct. 15, 2001

(86) PCT No.: PCT/GB01/04590

§ 371 (c)(1),
(2), (4) Date: Jan. 6, 2004

(87) PCT Pub. No.: WO02/32907

PCT Pub. Date: Apr. 25, 2002

(65) Prior Publication Data

US 2004/0116719 A1    Jun. 17, 2004

(30) Foreign Application Priority Data

Oct. 16, 2000 (GB) .................................. 0025313.8

(51) Int. Cl.
*C07D 321/00* (2006.01)
(52) U.S. Cl. ........................................ 549/348; 549/350
(58) Field of Classification Search ................ 549/348, 549/350
See application file for complete search history.

(56) References Cited

U.S. PATENT DOCUMENTS

| 5,395,951 | A | 3/1995 | Nagasampagi et al. ..... 549/383 |
|---|---|---|---|
| 5,827,521 | A | 10/1998 | Moorty et al. ............... 424/405 |
| 5,856,526 | A | 1/1999 | Sankaram et al. .......... 549/348 |
| 6,312,738 | B1 * | 11/2001 | O'Shea et al. .............. 424/761 |

FOREIGN PATENT DOCUMENTS

| EP | 0 581 467 | 9/1996 |
|---|---|---|
| EP | 0 834 254 A1 | 4/1998 |
| EP | 0 617 119 | 8/2000 |
| WO | WO9639845 | 12/1996 |
| WO | WO9902533 | 1/1999 |
| WO | WO02/32907 | 4/2002 |

OTHER PUBLICATIONS

GB 0025313.8 Search Report (Sep. 17, 2001).
GB 9924256.2 Search Report (Feb. 9, 2000).
PCT/GB01/04590 International Search Report (Feb. 6, 2002).

* cited by examiner

*Primary Examiner*—Joseph K. McKane
*Assistant Examiner*—Robert Shiao
(74) *Attorney, Agent, or Firm*—Williams, Morgan & Amerson, P.C.

(57) ABSTRACT

There is disclosed a method for treating a source of azadirachtin: (a) dissolving said sample in an organic polar solvent; (b) combining the solution of step (a) with an organic non-polar solvent to form a single phase containing the said solvents and dissolved sample; (c) treating said single phase of step (b) with an aqueous salt solution to form an aqueous phase and a phase containing the organic non-polar solvent; and (d) recovering one or other or both of the aqueous phase and the phase containing the organic polar solvent.

18 Claims, No Drawings

EXTRACTION METHOD

This application is a 371 of PCT/GB01/04590 filed on Oct. 15, 2001.

This invention relates to a method of treating an impure sample of azadirachtin isolated from a natural source to increase its purity.

Azadirachtin A (normally simply referred to as azadirachtin) is present throughout the Neem tree (*Azadirachta Indica*) and in significant quantities of up to 0.8% in the seed and is well known for its potentially wide ranging beneficial properties including insecticidal properties. Azadirachtin has been found to occur in several other plants which include the Chinaberry Tree and the Babool Bush. In addition, several hundred compounds have been identified in the Neem Tree, many occurring in the seed including the 12 main triterpenoids which include nimbin, salannin and 3-tigloylazadirachtol (also known as azadirachtin B). Several of these compounds have been shown to have beneficial pharmaceutical and insecticidal properties. The table at the end of this description contains a list of the phytochemicals of *Azadirachta Indica* and their location (bark, seed, etc.)

Methods are known in which the neem seed (or other azadirachtin source) is processed, including solvent extraction steps to obtain a crude solid extract containing the azadirachtin; typically such known processes (e.g. U.S. Pat. No. 5,856,526) result in a product containing normally up to 15% azadirachtin and occasionally 25–30%. In order to isolate pure azadirachtin A (e.g. above about 90% purity), expensive chromatographic methods are normally used. As a result azadirachtin with a purity of 80% currently retails for about US$ 85,000 per gram.

The present invention provides a novel solvent extraction process whereby the purity of a crude sample of azadirachtin can be increased, potentially up to a purity in excess of 90%, without the need to resort to chromatographic methods. The process may also enable the other potentially valuable by-products such as nimbin, salannin and gedunin associated with the natural sources of azadirachtin to be concentrated and isolated.

According to a first aspect of the present invention, there is provided a method for treating a source of azadirachtin:

(a) dissolving said sample in an organic polar solvent;

(b) combining the solution of step (a) with an organic non-polar solvent to form a single phase containing the said solvents and dissolved sample;

(c) treating said single phase of step (b) with an aqueous salt solution to form an aqueous phase and a phase containing the organic non-polar solvent; and (d) recovering one or other or both of the aqueous phase and the phase containing the organic polar solvent.

When, as will normally be the case, the aqueous phase is recovered, it may be treated to isolate an azadirachtin-containing component therefrom. Alternatively, as described in more detail below, it may be pooled with subsequent washings of the recycled organic non-polar phase and then treated to separate the azadirachtin-containing component therefrom.

It has been found that, when a crude sample of azadirachtin is treated in accordance with this method aspect of the invention, an equilibrium is established between the organic and aqueous phases in which the azadirachtin A, D, E and I and, it is believed, also the gedunin preferentially accumulate as either a syrup-like or solid material (depending on the stage of purification) which is found in the aqueous layer or phase of step (c). The azadirachtin B, nimbin and salannin preferentially accumulate in the organic non-polar layer. This provides a means whereby the various compounds in the starting sample can be separated from each other and enriched.

The method of the present invention may be used to isolate any one or more of the different components of natural azadirachtin sources such as the neem seed. Although this would normally include isolation of the azadirachtin A, which is an extremely valuable natural product when in the pure form, it is not necessarily the case that the azadirachtin A will be isolated in all embodiments of the invention; thus, in some embodiments of the invention the method may be carried out to isolate other components of the neem seed.

In preferred embodiments of the method of this aspect of the invention, the non-polar organic phase in step (c) is recovered and subjected again to the treatment of step (c). This treatment of the non-polar organic phase with the aqueous salt solution may be repeated several times until no more solid matter is observed accumulating in the aqueous phase. This may require, for example, up to 10 cycles, typically up to 5 cycles. The azadirachtin-containing component may be isolated from the aqueous phase at the end of each cycle and combined; alternatively, the recovered aqueous phases from each cycle may be pooled and, if desired at this stage, the azadirachtin-containing component may be isolated. Starting with a 30% purity sample, and after cycling in this way, the solid product obtained may typically contain about 45% azadirachtin A.

Where the starting sample has a low concentration of azadirachtin (e.g. 5–10%), it may be desirable, rather than recycling the organic non-polar phase, to isolate the solid azadirachtin-containing sample from the aqueous phase and recycle this through process steps (a)–(c). This may be carried out several times until the concentration of azadirachtin in the solid material reaches a concentration of about 40%.

The azadirachtin-containing sample which is subjected to the method of the present invention may be one which contains at least 10% azadirachtin, and thus results from a preliminary processing of the natural source (which may contain varying amounts of the various compounds of interest depending on the quality of the seed or other source) in order to increase the azadirachtin content to that level. The better the purity of the starting azadirachtin, the fewer cycles are required to achieve a high purity material. Good results may be obtained using, as the starting material for the process of the invention, an azadirachtin-containing sample in which the azadirachtin content is of the order of 25–30%. As an alternative, it has been found that the process of the present invention may be used to purify a sample taken direct from the neem seed (or other primary source of azadirachtin), i.e. with no preliminary processing. This provides a valuable alternative to the use of the conventional preliminary processing steps of a primary source of azadirachtin.

Where a conventional initial extraction method is used, the precise nature of this is not crucial to the present invention, although it is noted that different initial extraction methods result in different concentrations of the various compounds of interest in the resulting product. An example of a preliminary processing method has the following steps:

1. Preparation of the seed by air drying in the shade and separation of the seed from the pulp. It is important not to dry in the full sun light as this may cause the azadirachtin to break down.

2. Grinding of the dried seed with a solvent to remove the oil. Neem seed can contain up to 50% oil which must be removed using a suitable solvent such as hexane. The neem oil is separated from the solvent which is recovered and the oil retained for sale, further processing or formulation.

3. Soaking of the seed cake in a polar solvent such as methanol for an extended period of up to 24 hours without the application of heat and with slow stirring. The use of heat tends to cause the break down of the azadirachtin. Repeat extraction three times to maximise the amount of compounds in the extract.

4. Separation of the methanol liquid containing the useful compounds including azadirachtin from the seed cake. Separation may be by any suitable means including filtration under vacuum.

5. Remove up to 80% of the methanol under reduced pressure to produce a thick syrup. Water is then added to the syrup.

6. Add dichloromethane in the ratio of about 4:3 parts of syrup mixture. Stir for up to 45 minutes then allow to settle into two layers. The lower dichloromethane layer is removed for further processing and the aqueous layer is treated with the same volume of dichloromethane in the ratio 4:3. The extraction is completed at least 3 times to ensure complete removal of azadirachtin from the syrup.

7. All the dichloromethane layers are combined and dried with a suitable drying agent such as magnesium sulphate. The drying agent is removed by filtration and dichloromethane recovered. The extract is treated with twice its weight of hexane to form a precipitate, which is recovered by filtering. The precipitate then typically contains approximately 5%–15% azadirachtin.

In step (a) of the method of the first aspect of this invention, the sample is dissolved in an organic polar solvent. Examples of suitable solvents include acetone, methanol and ethanol or mixtures thereof, with methanol or acetone being preferred. The amount of organic polar solvent used should be sufficient to dissolve the sample, but otherwise is not critical. An amount of 200 ml of solvent per 100 g of sample has been found to be satisfactory where the solvent is acetone or methanol. Typically, the material is added to the solvent and stirred for a sufficient time (e.g. 30 minutes) to dissolve the material. Any material which is insoluble may be removed, for example by filtration.

The solution of step (a) is then combined with an organic non-polar solvent to form a single phase which contains the said solvents and the dissolved material. The organic non-polar solvent used in this step is preferably a halogenated hydrocarbon, such as carbon tetrachloride, chloroform or dichloromethane. However, other non-polar solvents, such as toluene are also operable. The presently preferred non-polar solvent is carbon tetrachloride. An amount of the organic non-polar solvent at least equal to the amount of the organic polar solvent used in step (a) may be employed. Ratios of organic polar solvent to non-polar organic solvent up to 1:20 are operable, but preferred is about 1:2.

Typically, the single phase formed in step (b) is a brown to dark brown colour, depending on the purity of the starting material.

In step (c), the single phase of step (b) is treated with an aqueous salt solution. On the laboratory scale, this step may be carried out in a separating funnel to facilitate separation of the phases. The solutions should be thoroughly mixed and then allowed to separate to form two layers, an aqueous layer and a non-polar solvent layer below. A solid or syrupy material (depending upon the purity of the initial sample) separates in the aqueous layer.

Preferred salts are those which form a solution which is approximately neutral in pH (about 6.5–7.5) since basic or acid salt solutions may tend to cause the azadirachtin or other components to decompose. Preferred salts are the water soluble alkali metal and alkaline earth metal halides, with sodium chloride being particularly preferred. The salt solution is preferably non-saturated. A solution containing between about 5% and saturated is satisfactory, with a concentration of about 10% being optimum.

The volume of salt solution relative to the volume of the organic phase resulting from step (b) may range from 1:1 to 15:1. Preferred is a ratio of 2:1 by volume. The mixture should be thoroughly agitated or mixed and then allowed to stand long enough to achieve separation, for example for a period of time of the order of 30 minutes, to produce two layers. The upper layer is the aqueous salt layer and the lower layer is the organic non-polar layer. The layers are separated and it is preferred that the organic non-polar layer is then subjected to further cycles of treatment with salt solution until no more solid matter is observed to accumulate in the aqueous-phase, as described above. In the first salt solution washing, a dark brown syrupy substance appears in the aqueous phase. With repeated cycles this becomes whiter and less syrupy and the volume decreases.

The azadirachtin-containing component may be separated from the aqueous phase each cycle or the aqueous salt solution washings may be retained and combined and the solids recovered, for example by filtration. The recovered solid is normally a yellow/white powder and is enriched in azadirachtin relative to the starting material, for example up to about 45% azadirachtin.

The aqueous phase from each cycle, after removal of the azadirachtin-containing component may be recovered and retained for further processing to recover any water-soluble compounds of interest therefrom.

The organic non-polar phase may be retained and treated further. This material contains 3-tigloylazadirachtol (sometimes known as Aza B) and also a number of the other triterpenoids such as nimbin and salannin, as well as some other compounds.

In order to increase the purity of the azadirachtin-containing component separated from the aqueous phase still further, the recovered solid may be subjected to at least one further round of the process of the present invention. The same or different solvents may be used in the second and any further rounds. For example, in one experiment, good results have been obtained where, in the first round, methanol is used as the polar solvent, and, in the second round, acetone is used as the polar solvent.

As mentioned previously, the azadirachtin-containing component isolated from the aqueous phase in the process of the invention contains the compounds azadirachtin A, D, H and I. In order to purify this component further, the solid may be dissolved in a first solvent in which the various compounds are soluble, for example chloroform or ethyl acetate. The minimum amount to completely dissolve the solid material may be employed. To this solution is added a second solvent which is matched with the first solvent so as to give a precipitate of the dissolved compounds other than the azadirachtin A. Thus, where the first solvent is chloroform, the second solvent may be ether, for example in the ratio of approximately 1:3. Where the first solvent is ethyl acetate, the second solvent may be hexane. The first and second solvents are preferably low boiling point solvents so that they can be removed at a relatively low temperature which does not decompose any of the valuable compounds separated. A yellow to white solid is formed which contains mainly azadirachtin D, R and I, together with some azadirachtin A. This material can be retained for further separation of these triterpenoids if required. The chloroform/ether layer (or other combination of first and second solvent), contains the majority of the azadirachtin A from which it may be isolated. For example, the ether may be removed from the mixture and the chloroform reduced to approximately 20% of its original volume. The solvents may be recovered for reuse. To the concentrated solution may be added three times the volume of a solvent in which the azadirachtin A is insoluble and of low boiling point such as hexane, pentane or heptane, most preferably hexane to produce a white solid which may contain approximately 70% azadirachtin A. The hexane-rich filtrate may be recovered and recirculated.

The organic non-polar layer which may be recovered in step (c) of the process of the invention contains mainly the azadirachtin B with some azadirachtin A, salannin, nimbin and other similar compounds. This layer may, for example, be treated to remove at least 50% of the organic solvent under reduced pressure, and then treated with an equal volume of hexane. The majority of azadirachtin A and some azadirachtin B is precipitated, whilst the filtrate contains the majority of the azadirachtin B and other compounds.

At all stages the compounds are partitioned selectively between the two layers. Repeated reprocessing of the partitioned compounds causes the compounds to be concentrated giving purities in excess of 60% for the individual target compounds of interest.

At all stages the various fractions and solvents are recycled or recovered for reuse so reducing the overall cost of the extraction and purification.

In accordance with the process of the present invention, large quantities of pure azadirachtin A may be produced, which has hitherto proved impossible. Thus, in accordance with another aspect of the invention, there is provided a package containing at least 10 g of azadirachtin A having a purity of at least 50%. Any suitable packaging for the azadirachtin A product may be employed, such as plastic bags and glass, or plastic tubes. Preferably, the azadirachtin A in the package has a purity of at least 70%, preferably at least 90%. The package may contain at least 100 g of the pure azadirachtin A, preferably at least 100 g of azadirachtin A.

The invention will now be illustrated, by way of the following non-limiting example.

EXAMPLE

This example describes the methods and techniques used to purify azadirachtin A and B from a sample of technical azadirachtin with an initial concentration of 30% azadirachtin A. The example was worked on a weight sample of 200 grams.

Step 1.

Accurately weight 200 of technical grade Azadirachtin, analysis 33% azadirachtin A.

Step 2.

Dissolve in 400 mls of methanol at room temperature 18° C., stir until completely dissolved, which in this example takes about 15 minutes.

Step 3.

When fully dissolved and whilst still stirring 800 mls of carbon tetrachloride (ratio of 2:1 to the methanol) was added. The mixture was stirred for a further 10 minutes.

Step 4.

200 mls of 10% brine was added, and stirred as rapidly as possible using an overhead stirrer. Solid material was formed in the brine layer. The liquid was allowed to separate into two layers with the lower layer being the carbon tetrachloride layer. The two layers were separated using a separating funnel and the brine layer filtered to remove the precipitate. This precipitate was dried under vacuum until constant weight, usually about 2 hours. The weight obtained was 80 grams. An analysis sample was prepared by weighing 19 mg of the precipitate and dissolving in 19 ml acetonitrile (1:1). 100 µl of the solution was diluted with 5 ml of hlpc grade water. The sample was analysed by HPLC to give an azadirachtin A content of 56%.

Step 5.

A further 200 ml of the brine solution was added to the separated carbon tetrachloride layer, and the liquid rapidly stirred as before. A further precipitate was formed in the brine layer which is recovered as previously. The precipitate reduces in volume with each washing and its colour changes from yellow to white. The cycle is repeated until no further precipitate appears. This usually takes 4 to 5 washings. The carbon tetrachloride layer was retained for further treatment. This layer contained the azadirachtin B. The brine washings contained 21 grams of solid having an azadirachtin A content of 56%.

Step 6.

The process was repeated a third time by the addition of a further 200 ml of brine to the residual carbon tetrachloride layer of step 5. The solid formed was 46 grams and was found to have an azadirachtin A content of 69%.

Step 7.

The process was repeated a fourth time by the addition of a further 200 ml of brine to the residual carbon tetrachloride layer of step 6. The solid formed was 13 grams having an Azadirachtin A content of 58%.

Step 8.

The process was repeated a fifth time with the addition of 200 ml of brine to the residual carbon tetrachloride layer of step 7. No further solid was yielded. The carbon tetrachloride layer was dried with $MgSO_4$, filtered, reduced to ⅓ its volume and three times the volume of hexane added. A pale yellow solid formed weighing 12.3 grams. Analysis of this sample gave azadirachtin B at 46% and azadirachtin A at 26%.

Step 9.

All the brine water washings were combined and 500 ml of chloroform was added. The resultant mixture was stirred or otherwise mixed and then allowed to separate. The chloroform layer was separated, dried with $MgSO_4$, and the chloroform recovered to ⅓ volume. Hexane was added giving a solid which was removed by filtration. The solid yielded 15 grams giving 53% azadirachtin A content and 7% azadirachtin B.

This was the end of the first "loop".

Step 10.

The solid from the first four brine washings was added-together to give a total weight of 160 grams. This was dissolved in 320 ml of acetone and stirred until fully dissolved. After 15 minutes, 740 ml $CCl_4$ was added and stirred. The resulting solution was washed with 640 ml of 10% brine in 4 parts 160 ml each.

Step 11.

As with the initial addition of brine, solid formed in the brine layer which was separated and dried as previously. The first washing gave 28 grams azadirachtin A content 83%.

Step 12.

The second washing with 160 ml of brine produced 4 grams of solid having an Azadirachtin A content of 65%.

Step 13.

The washing was repeated as previously and the solid separated and dried to give a weight of 6.6 grams and an azadirachtin A content of 49%.

Step 14.

The fourth washing gave a syrup rather than a solid. This was dissolved in a minimum of chloroform and hexane added to give a white solid and yellow syrup. The white solid was filtered to give 18 grams of product having an azadirachtin A content of 40% and an azadirachtin B of 30%. The syrup was separated and dried to give a 10 g of a solid product (azadirachtin A 57%).

The total weight recovered at this point was 142 grams.

Step 15.

The samples from steps 11 onwards were combined and dissolved in chloroform to which ether was then added to form a solid. This was removed by filtering and drying to yield 28 grams of product.

Step 16.

The ether was removed from the filtrate by vacuum and five times the volume of hexane added. A white solid rich in azadirachtin A was obtained (azadirachtin A, 40 g, purity 70%). The filtrate was treated to precipitate 12 g of azadirachtin B material. The various washings were combined and 18 g of a precipitate containing azadirachtin A and azadirachtin B was obtained.

The 28 grams of azadirachtin A of over 80% purity from step 15 was retained and the various fractions with a lower azadirachtin content were re-circulated by adding to fresh technical grade material and reprocessed. In this way the concentration of the azadirachtin A was increased until it reached the required level. Similarly with the azadirachtin B, this was recycled until the required concentration was obtained.

Neem seed extract contains many different compounds in addition to the Azadirachtin A and B. These include Azadirachtin D, H, I, Nimbin and salannin. The process concentrates some of these compounds in the brine layer and some in the carbon tetrachloride layer allowing their separation and purification.

TABLE

| | |
|---|---|
| 1-TIGLOYL-3-ACETYL-11-METHOXY-AZADIRACHTININ | Bark |
| 1ALPHA-METHOXY-1,2-DIHYDROAZADIRADIONE | Seed |
| 1BETA, 2BETA-DIEPOXY-AZADIRADIONE | Seed |
| 3-ACETYL-7-TIGLOYL-LACTONE-VILASININ | Leaf |
| 3-DESACETYL-3-CINNAMOYL-AZADIRACHTIN | Leaf |
| 3-DEACETYL-SALININ | Leaf |
| 3-DESACETYLSALANNIN | Seed |
| 3-TIGLOYLZAZDIRACHLOL | Seed |
| 4-EPINIMBIN | Seed |
| 4ALPHA, 6ALPHA-DIHYDROXY-A-HOMO-AZADIRADIONE | Leaf |
| 6-ACETYL-NIMBANDIOL | Seed |
| 6-DESACETYLNIMBINENE | Bark |
| 6-DESACETYLNIMBINENE | Leaf |
| 6-DESACETYLNIMBINENE | Seed |
| 6-O-ACETYL-NIMBANDIOL | Plant |

TABLE-continued

| | |
|---|---|
| 7-ACETYLNEOTRICHILENONE | Seed |
| 7-DESACETYL-7-BENZOYL-AZADIRADIONE | Seed |
| 7-DESACETYL-7-BENZOYLEPOXY-AZADIRADIONE | Seed |
| 7-DESACETYL-7-HYDROXY-AZADIRADIONE | Fruit |
| 7-DESACETYL-GEDUNIN | Seed |
| 17-BETA-HYDROXYAZADIRDIONE | Seed |
| 17-EPIAZADIRADIONE | Seed |
| 22,23-DIHYDRO-23BETA-METHOXY-AZADIRACHTIN | Seed |
| ARACHIDIC-ACID | Fruit |
| ASH | Fruit |
| ASH | Leaf |
| AZADIRACHTANIN | Leaf |
| AZADIRACHTANIN-A | Leaf |
| AZADIRACHTIN | Seed |
| AZADIRACHTOL | Fruit |
| AZADIRADIONE | Seed |
| AZADIRONE | Seed |
| BEHENIC-ACID | Fruit |
| BETA-SITOSTEROL | Flower |
| BETA-SITOSTEROL | Leaf |
| CALCIUM | Fruit |
| CALCIUM | Leaf |
| CARBOHYDRATES | Fruit |
| CARBOHYDRATES | Leaf |
| DESACETYLNIMBIN | Stem Bark |
| EO | Stem Bark |
| EPOXYAZADIRADIONE | Seed |
| FAT | Fruit |
| FAT | Fruit |
| FAT | Seed |
| FIBER | Leaf |
| GEDUNIN | Seed |
| HYPEROSIDE | Leaf |
| ISOAZADIROLIDE | Leaf |
| ISOMARGOSINOLIDE | Plant |
| ISONIMBINOCINOLIDE | Plant |
| ISONIMBINOLIDE | Stem Bark |
| ISONIMBOCINOLIDE | Leaf |
| ISONIMOLICINOLIDE | Fruit |
| KAEMPFEROL | Flower |
| LIGNOCERIC-ACID | Fruit |
| LINOLEIC-ACID | Fruit |
| MAGNESIUM | Fruit |
| MAGNESIUM | Leaf |
| MARGODUNOLIDE | Plant |
| MARGOSINE | Stem Bark |
| MARGOSINOLIDE | Plant |
| MELDENIN | Seed |
| MELIANTRIOL | Seed |
| MYRICETIN | Flower |
| MYRISTIC-ACID | Fruit |
| NIMBAFLAVONE | Leaf |
| NIMBANDIOL | Leaf |
| NIMBANDIOL | Stem |
| NIMBIDIN | Seed |
| NIMBIDIN | Stem Bark |
| NIMBIN | Stem Bark |
| NIMBINENE | Bark |
| NIMBINENE | Leaf |
| NIMBINENE | Stem |
| NIMBININ | Stem Bark |
| NIMBINONE | Stem Bark |
| NIMBIOL | Bark |
| NIMBIONE | Stem Bark |
| NIMBOCINOLIDE | Plant |
| NIMBOCINOME | Plant |
| NIMBOLIDE | Leaf |
| NIMBOLIN-A | Wood |
| NIMBOLIN-B | Wood |
| NIMBOSTEROL | Stem Bark |
| NIMOCINOL | Fruit |
| NIMOLICINOIC-ACID | Fruit |
| NIMOLICINOL | Seed |
| NIMOLINONE | Fruit |
| NONACOSANE | Flower |
| OLEIC-ACID | Fruit |
| PALMITIC-ACID | Fruit |
| PHOSPHORUS | Fruit |
| PHOSPHORUS | Leaf |

TABLE-continued

| | |
|---|---|
| PROTEIN | Fruit |
| PROTEIN | Leaf |
| QUERCETIN | Flower |
| QUERCETIN | Leaf |
| QUERCITRIN | Leaf |
| RESIN | Seed |
| RUTIN | Leaf |
| SALANNIN | Seed |
| SALANNOLIDE | Plant |
| SCOPOLETIN | Plant |
| STEARIC-ACID | Fruit |
| SUGIOL | Bark |
| SULFUR | Seed |
| TANNIN | Stem Bark |
| VEPININ | Seed |
| VILASANIN | Leaf |

The invention claimed is:

1. A method for extracting azadirachtin from an azadirachtin-containing sample, comprising:
   (a) dissolving said sample in an organic polar solvent;
   (b) combining the solution of step (a) with an organic non-polar solvent to form a single phase containing the said solvents and dissolved sample;
   (c) treating said single phase of step (b) with an aqueous salt solution to form an aqueous phase and a phase containing the organic non-polar solvent;
   (d) recovering the aqueous phase; and
   (e) treating the recovered aqueous phase to isolate an azadirachtin A component therefrom.

2. A method according to claim 1, wherein both the aqueous phase and the organic non-polar phases are recovered and the recovered organic non-polar phase treated in accordance with steps (c) and (d) of claim 1.

3. A method according to claim 2, wherein the recycling of the organic non-polar phase is carried out a plurality of times.

4. A method according to claim 3, wherein the aqueous phase in each cycle is recovered and then pooled with each other prior to isolation of a solid product therefrom.

5. A method according to claim 1, wherein, the organic polar solvent in step (a) is selected from acetone, methanol and ethanol or mixtures thereof.

6. A method according to claim 1, wherein the organic non-polar solvent used in step (b) is a halogenated hydrocarbon.

7. A method according to claim 6, wherein the organic non-polar solvent is toluene, carbon tetrachloride, chloroform or dichloromethane.

8. A method according to claim 1, wherein the single phase of step (b) is treated with a non-saturated aqueous salt solution.

9. A method according to claim 1, wherein the aqueous salt solution is a solution of a salt which forms a solution which is approximately neutral in pH.

10. A method according to claim 9, wherein the salt is selected from water soluble alkali metal and alkaline earth metal halides.

11. A method according to claim 10, wherein the salt is sodium chloride.

12. A method according to claim 1, wherein the salt solution contains at least about 5% salt by weight.

13. A method according to claim 1, wherein the organic non-polar phase is recovered and treated to isolate an azadirachtin B component.

14. A method according to claim 2, wherein the organic non-polar phase, after further treatment in accordance with steps (c) and (d), is recovered and treated to isolate an azadirachtin B component.

15. A method for extracting azadirachtin from an azadirachtin-containing sample, comprising:
   (a) dissolving said sample in an organic polar solvent;
   (b) combining the solution of step (a) with an organic non-polar solvent to form a single phase containing the said solvents and dissolved sample;
   (c) treating said single phase of step (b) with an aqueous salt solution to from an aqueous phase and a phase containing the organic non-polar solvent;
   (d) recovering the phase containing the organic non-polar solvent;
   (e) treating the recovered organic non-polar phase to isolate an azadirachtin B component therefrom.

16. A method according to claim 15, further comprising recovering the aqueous phase.

17. A method according to claim 15, further comprising treating the recovered organic non-polar phase in accordance with steps (c) and (d) prior to step (e).

18. A method according to claim 17, wherein the treating of the organic non-polar phase in accordance with steps (c) and (d) is carried out a plurality of times.

* * * * *